(12) United States Patent
Peterson

(10) Patent No.: US 10,159,548 B2
(45) Date of Patent: Dec. 25, 2018

(54) DENTAL CURING LIGHT

(71) Applicant: Garrison Dental Solutions, L.L.C., Spring Lake, MI (US)

(72) Inventor: Steven H. Peterson, Martin, MI (US)

(73) Assignee: Garrison Dental Solutions, L.L.C., Spring Lake, MI (US)

( * ) Notice: Subject to any disclaimer, the term of this patent is extended or adjusted under 35 U.S.C. 154(b) by 274 days.

(21) Appl. No.: 14/857,273

(22) Filed: Sep. 17, 2015

(65) Prior Publication Data

US 2016/0074144 A1    Mar. 17, 2016

Related U.S. Application Data

(60) Provisional application No. 62/051,472, filed on Sep. 17, 2014.

(51) Int. Cl.
*A61C 1/00* (2006.01)
*A61C 13/15* (2006.01)

(52) U.S. Cl.
CPC .................. *A61C 19/004* (2013.01)

(58) Field of Classification Search
CPC ........................ A61C 19/004; A61C 19/003
See application file for complete search history.

(56) References Cited

U.S. PATENT DOCUMENTS

| | | |
|---|---|---|
| 3,638,312 A | 2/1972 | Szwarc et al. |
| 4,223,680 A | 9/1980 | Jöbsis |
| 4,309,617 A | 1/1982 | Long |
| 4,385,344 A | 5/1983 | Gonser |
| 4,445,858 A | 5/1984 | Johnson |
| 4,450,139 A | 5/1984 | Bussiere et al. |
| 4,716,296 A | 12/1987 | Bussière et al. |
| 4,818,231 A | 4/1989 | Steiner et al. |
| 4,888,489 A | 12/1989 | Bryan |
| 4,924,070 A | 5/1990 | Friedman |
| 4,948,215 A | 8/1990 | Friedman |
| 4,952,143 A | 8/1990 | Becker et al. |
| 5,147,204 A | 9/1992 | Patten et al. |
| 5,184,044 A | 2/1993 | Thomas |

(Continued)

FOREIGN PATENT DOCUMENTS

| | | |
|---|---|---|
| CA | 2 295 056 | 1/1999 |
| CA | 2 319 890 | 3/2001 |

(Continued)

OTHER PUBLICATIONS

Karaarslan, E., et al., "Assessment of changes in color and color parameters of light-cured composite resin after alternative polymerization methods", European Journal of Dentistry, Jan. 2013, vol. 7, pp. 110-116.

(Continued)

*Primary Examiner* — Nicholas Lucchesi
(74) *Attorney, Agent, or Firm* — Warner Norcross + Judd LLP

(57) ABSTRACT

An optical sensor for an instrument to form a closed-loop curing instrument that is configured to manage the quantity of delivered energy to a curable material, including a composite restoration for a tooth. The closed-loop curing instrument is configured to analyze a signal indicative of the light reflecting from the curable material, and to adjust light output based on the analysis.

18 Claims, 6 Drawing Sheets

(56) References Cited

U.S. PATENT DOCUMENTS

| | | |
|---|---|---|
| 5,201,655 A | 4/1993 | Friedman |
| 5,290,169 A | 3/1994 | Friedman et al. |
| 5,316,473 A | 5/1994 | Hare |
| 5,397,892 A | 3/1995 | Abdelqader |
| 5,415,543 A | 5/1995 | Rozmajzl, Jr. |
| 5,471,129 A | 11/1995 | Mann |
| 5,487,662 A | 1/1996 | Kipke et al. |
| 5,554,855 A | 9/1996 | Ueno |
| 5,616,141 A | 4/1997 | Cipolla |
| 5,634,711 A | 6/1997 | Kennedy et al. |
| 5,738,678 A | 4/1998 | Patel |
| 5,749,724 A | 5/1998 | Cheng |
| 5,759,030 A * | 6/1998 | Jung .................. A61B 5/4547 356/405 |
| 5,759,032 A | 6/1998 | Bartel |
| 5,803,729 A | 9/1998 | Tsimerman |
| 5,879,159 A | 3/1999 | Cipolla |
| 5,912,470 A | 6/1999 | Eibofner et al. |
| 5,975,895 A | 11/1999 | Sullivan |
| 6,065,965 A | 5/2000 | Rechmann |
| 6,068,474 A | 5/2000 | Senn et al. |
| 6,089,740 A | 7/2000 | Forehand et al. |
| 6,095,812 A | 8/2000 | Senn et al. |
| 6,102,696 A | 8/2000 | Osterwalder et al. |
| 6,103,203 A | 8/2000 | Fischer |
| 6,123,545 A | 9/2000 | Eggler et al. |
| 6,159,005 A | 12/2000 | Herold et al. |
| 6,168,431 B1 | 1/2001 | Narusawa et al. |
| 6,171,105 B1 | 1/2001 | Sarmadi |
| 6,193,510 B1 | 2/2001 | Tsimerman |
| 6,200,134 B1 | 3/2001 | Kovac et al. |
| 6,208,788 B1 | 3/2001 | Nosov |
| 6,254,385 B1 * | 7/2001 | Jung .................. A61B 5/0088 356/405 |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,325,791 B1 | 12/2001 | Shimoji |
| 6,331,111 B1 | 12/2001 | Cao |
| 6,382,967 B1 | 5/2002 | Robner et al. |
| 6,419,483 B1 | 7/2002 | Adam et al. |
| 6,435,872 B1 | 8/2002 | Nagel |
| 6,440,122 B1 | 8/2002 | Shimoji |
| 6,456,895 B1 | 9/2002 | Aloisio, Jr. et al. |
| 6,468,077 B1 | 10/2002 | Melikechi et al. |
| 6,482,004 B1 | 11/2002 | Senn et al. |
| 6,485,301 B1 | 11/2002 | Gemunder et al. |
| 6,511,317 B2 | 1/2003 | Melikechi et al. |
| 6,514,075 B1 | 2/2003 | Jacob |
| 6,522,086 B2 | 2/2003 | Gemunder et al. |
| 6,602,074 B1 | 8/2003 | Suh et al. |
| 6,611,110 B1 | 8/2003 | Fregoso |
| 6,688,763 B2 | 2/2004 | Pameijer et al. |
| 6,692,250 B1 | 2/2004 | Decaudin et al. |
| 6,692,252 B2 | 2/2004 | Scott |
| 6,695,614 B2 | 2/2004 | Plank |
| 6,702,576 B2 | 3/2004 | Fischer et al. |
| 6,709,128 B2 | 3/2004 | Gordon et al. |
| 6,719,559 B2 | 4/2004 | Cao |
| 6,741,410 B2 | 5/2004 | Plank et al. |
| 6,750,971 B2 | 6/2004 | Overbeck et al. |
| 6,755,647 B2 | 6/2004 | Melikechi et al. |
| 6,759,661 B1 | 7/2004 | Baggett et al. |
| 6,767,109 B2 | 7/2004 | Plank et al. |
| 6,783,362 B2 | 8/2004 | Cao |
| 6,793,490 B2 | 9/2004 | Bianchetti et al. |
| 6,799,967 B2 | 10/2004 | Cao |
| 6,824,294 B2 | 11/2004 | Cao |
| 6,857,873 B2 | 2/2005 | Bianchetti et al. |
| 6,880,954 B2 | 4/2005 | Ollett et al. |
| 6,890,175 B2 | 5/2005 | Fischer et al. |
| 6,893,258 B1 | 5/2005 | Kert |
| 6,910,886 B2 | 6/2005 | Cao |
| 6,918,762 B2 | 7/2005 | Gill et al. |
| 6,926,524 B2 | 8/2005 | Cao |
| 6,929,472 B2 | 8/2005 | Cao |
| 6,932,599 B1 | 8/2005 | Hartung |
| 6,932,600 B2 | 8/2005 | Cao |
| 6,940,659 B2 | 9/2005 | McLean et al. |
| 6,953,339 B1 | 10/2005 | Daffurn |
| 6,953,340 B2 | 10/2005 | Cao |
| 6,954,270 B2 | 10/2005 | Ostler et al. |
| 6,955,537 B2 | 10/2005 | Cao |
| 6,957,907 B2 | 10/2005 | Fischer et al. |
| 6,969,253 B2 | 11/2005 | Cao |
| 6,969,254 B2 | 11/2005 | Plank et al. |
| 6,971,876 B2 | 12/2005 | Cao |
| 6,974,319 B2 | 12/2005 | Cao |
| 6,976,841 B1 | 12/2005 | Osterwalder |
| 6,979,193 B2 | 12/2005 | Cao |
| 6,979,194 B2 | 12/2005 | Cao |
| 6,988,890 B2 | 1/2006 | Cao |
| 6,991,356 B2 | 1/2006 | Tsimerman et al. |
| 6,991,456 B2 | 1/2006 | Plank |
| 6,994,546 B2 | 2/2006 | Fisher et al. |
| 7,001,057 B2 | 2/2006 | Plank et al. |
| 7,004,755 B2 | 2/2006 | Seghatol |
| 7,029,277 B2 | 4/2006 | Gofman et al. |
| 7,050,168 B2 | 5/2006 | Overbeck et al. |
| 7,056,116 B2 | 6/2006 | Scott et al. |
| 7,066,732 B2 | 6/2006 | Cao |
| 7,074,040 B2 | 7/2006 | Kanca |
| 7,077,648 B2 | 7/2006 | Cao |
| 7,086,858 B2 | 8/2006 | Cao |
| 7,094,054 B2 | 8/2006 | Cao |
| 7,094,057 B2 | 8/2006 | Friedman |
| 7,097,364 B2 | 8/2006 | Wang |
| 7,101,072 B2 | 9/2006 | Takada et al. |
| 7,104,793 B2 | 9/2006 | Senn et al. |
| 7,106,523 B2 | 9/2006 | McLean et al. |
| 7,108,504 B2 | 9/2006 | Cao |
| 7,119,515 B2 | 10/2006 | Senn et al. |
| 7,125,249 B1 | 10/2006 | Lauren |
| 7,144,250 B2 | 12/2006 | Fischer et al. |
| 7,166,627 B2 | 1/2007 | Day et al. |
| 7,192,276 B2 | 3/2007 | Fischer et al. |
| 7,195,482 B2 | 3/2007 | Scott |
| 7,202,490 B2 | 4/2007 | Aguierre et al. |
| 7,210,814 B2 | 5/2007 | Scott et al. |
| 7,210,930 B2 | 5/2007 | Kovac et al. |
| 7,245,371 B2 | 7/2007 | Wang et al. |
| 7,252,678 B2 | 8/2007 | Ostler et al. |
| 7,267,457 B2 | 9/2007 | Ostler et al. |
| 7,267,546 B2 | 9/2007 | Scott et al. |
| 7,273,369 B2 | 9/2007 | Rosenblood et al. |
| 7,275,931 B2 | 10/2007 | Katsuda et al. |
| 7,283,230 B2 | 10/2007 | Ostler et al. |
| 7,294,364 B2 | 11/2007 | Cao |
| 7,311,722 B2 | 12/2007 | Larsen |
| 7,344,280 B2 | 3/2008 | Panagotacos et al. |
| 7,354,269 B2 | 4/2008 | Duret et al. |
| 7,407,616 B2 | 8/2008 | Melikechi et al. |
| 7,485,116 B2 | 2/2009 | Cao |
| 7,514,239 B2 | 4/2009 | Paszty et al. |
| 7,535,184 B1 | 5/2009 | Fregoso |
| 7,677,888 B1 | 3/2010 | Halm |
| 7,684,036 B2 | 3/2010 | Li et al. |
| 7,704,074 B2 | 4/2010 | Jensen |
| 7,766,654 B2 | 8/2010 | Plank et al. |
| 7,789,661 B2 | 9/2010 | Ostler et al. |
| 7,857,619 B2 | 12/2010 | Liu |
| 7,976,307 B2 | 7/2011 | Plank et al. |
| 7,989,839 B2 | 8/2011 | Dahm |
| 7,995,195 B2 | 8/2011 | Feichtinger et al. |
| 8,002,546 B2 | 8/2011 | Viscomi |
| 8,106,600 B1 | 1/2012 | Fregoso |
| 8,113,830 B2 | 2/2012 | Gill et al. |
| 8,113,831 B2 | 2/2012 | Plank et al. |
| 8,142,188 B2 | 3/2012 | Plank et al. |
| 8,231,383 B2 | 7/2012 | Gill et al. |
| 8,337,200 B2 | 12/2012 | Wang et al. |
| 8,337,201 B1 | 12/2012 | Mace |
| 8,366,441 B2 | 2/2013 | Swift |
| 8,382,472 B2 | 2/2013 | Plank et al. |

(56) References Cited

U.S. PATENT DOCUMENTS

| | | | |
|---|---|---|---|
| RE44,046 E | 3/2013 | Burtscher et al. |
| 8,469,707 B2 | 6/2013 | Emde |
| 8,568,140 B2 | 10/2013 | Kovac et al. |
| 8,632,235 B2 | 1/2014 | Senn |
| 8,679,796 B2 | 3/2014 | Carvalho Fernandes De Miranda Reis et al. |
| 8,900,851 B2 | 12/2014 | Cao |
| 8,905,748 B2 | 12/2014 | Cao et al. |
| 9,012,399 B2 | 4/2015 | Cao et al. |
| 9,012,531 B2 | 4/2015 | Abuelyaman et al. |
| 9,056,043 B2 | 6/2015 | Joly et al. |
| 9,144,479 B2 | 9/2015 | Sun et al. |
| 9,693,845 B2 | 7/2017 | Price |
| 9,757,207 B2 | 9/2017 | Pruckner et al. |
| 9,827,081 B2 | 11/2017 | Mecher |
| 2002/0115037 A1 | 8/2002 | Cao |
| 2002/0168603 A1 | 11/2002 | Cao |
| 2002/0168607 A1 | 11/2002 | Cao |
| 2002/0175628 A1 | 11/2002 | Cao |
| 2002/0182563 A1 | 12/2002 | Boutoussov et al. |
| 2002/0188218 A1 | 12/2002 | Lipman |
| 2003/0008260 A1 | 1/2003 | Wang et al. |
| 2003/0036031 A1 | 2/2003 | Lieb et al. |
| 2003/0081430 A1 | 5/2003 | Becker |
| 2003/0147258 A1 | 8/2003 | Fischer et al. |
| 2003/0148242 A1 | 8/2003 | Fischer et al. |
| 2003/0152885 A1 | 8/2003 | Dinh |
| 2003/0153903 A1 | 8/2003 | Kumagi et al. |
| 2003/0215766 A1 | 11/2003 | Fischer et al. |
| 2003/0219693 A1 | 11/2003 | Cao |
| 2003/0235800 A1 | 12/2003 | Qadar |
| 2004/0033465 A1 | 2/2004 | Otsuka |
| 2004/0051482 A1 | 3/2004 | Fregoso |
| 2004/0101802 A1 | 5/2004 | Scott |
| 2004/0120146 A1 | 6/2004 | Ostler et al. |
| 2004/0120151 A1 | 6/2004 | Ostler et al. |
| 2004/0152038 A1 | 8/2004 | Kumagai et al. |
| 2004/0164670 A1 | 8/2004 | Nanni et al. |
| 2004/0214131 A1 | 10/2004 | Fischer et al. |
| 2004/0229186 A1 | 11/2004 | Slone |
| 2004/0234923 A1 | 11/2004 | Larsen et al. |
| 2005/0048436 A1 | 3/2005 | Fishman et al. |
| 2005/0064361 A1 | 3/2005 | Benedicenti |
| 2005/0069503 A1 | 3/2005 | Larsen et al. |
| 2005/0074722 A1 | 4/2005 | Larsen et al. |
| 2005/0074723 A1 | 4/2005 | Ostler et al. |
| 2005/0085403 A1 | 4/2005 | Larsen et al. |
| 2005/0089482 A1 | 4/2005 | Larsen et al. |
| 2005/0136373 A1 | 6/2005 | Fischer et al. |
| 2005/0158687 A1 | 7/2005 | Dahm |
| 2005/0236586 A1 | 10/2005 | Hartung |
| 2006/0018123 A1 | 1/2006 | Rose |
| 2006/0033052 A1 | 2/2006 | Scott |
| 2006/0040231 A1 | 2/2006 | Quan et al. |
| 2006/0076517 A1 | 4/2006 | Wang |
| 2006/0084028 A1 | 4/2006 | Cheetham et al. |
| 2006/0115783 A1 | 6/2006 | McLaren |
| 2006/0134576 A1 | 6/2006 | West |
| 2006/0134577 A1 | 6/2006 | Zuk |
| 2006/0188835 A1 | 8/2006 | Nagel et al. |
| 2006/0199144 A1 | 9/2006 | Liu et al. |
| 2006/0252005 A1 | 11/2006 | Feinbloom et al. |
| 2006/0275732 A1 | 12/2006 | Cao |
| 2006/0275733 A1 | 12/2006 | Cao |
| 2007/0020578 A1 | 1/2007 | Scott et al. |
| 2007/0037113 A1 | 2/2007 | Scott et al. |
| 2007/0054234 A1 | 3/2007 | Oxman et al. |
| 2007/0128577 A1 | 6/2007 | Scott et al. |
| 2007/0190479 A1 | 8/2007 | Jackson, III et al. |
| 2007/0224570 A1 | 9/2007 | West et al. |
| 2007/0259309 A1 | 11/2007 | West et al. |
| 2008/0032252 A1 | 2/2008 | Hayman et al. |
| 2008/0057463 A1 | 3/2008 | Wong et al. |
| 2008/0166677 A1 | 7/2008 | Graham |
| 2008/0220389 A1 | 9/2008 | Wang |
| 2008/0268401 A1 | 10/2008 | Kim |
| 2008/0274436 A1 | 11/2008 | West et al. |
| 2008/0285302 A1 | 11/2008 | Scott et al. |
| 2008/0311545 A1 | 12/2008 | Ostler et al. |
| 2009/0046476 A1 | 2/2009 | West et al. |
| 2009/0208894 A1 | 8/2009 | Orloff et al. |
| 2009/0227875 A1 | 9/2009 | Cao et al. |
| 2009/0233254 A1 | 9/2009 | Hayman et al. |
| 2009/0322227 A1 | 12/2009 | Jones et al. |
| 2009/0323733 A1 | 12/2009 | Charkas |
| 2009/0324536 A1 | 12/2009 | Sun et al. |
| 2010/0003633 A1 | 1/2010 | Senn et al. |
| 2010/0075272 A1 | 3/2010 | Lin et al. |
| 2010/0140450 A1 | 6/2010 | Duret et al. |
| 2010/0167226 A1 | 7/2010 | Altshuler et al. |
| 2010/0176729 A2 | 7/2010 | Jones et al. |
| 2010/0190130 A1 | 7/2010 | LaRocque |
| 2010/0216089 A1 | 8/2010 | Cao |
| 2010/0254149 A1 | 10/2010 | Gill |
| 2010/0273123 A1 | 10/2010 | Mecher |
| 2011/0141733 A1 | 6/2011 | Senn |
| 2011/0151401 A1 | 6/2011 | Jensen |
| 2011/0165681 A1 | 7/2011 | Boyden et al. |
| 2011/0236851 A1 | 9/2011 | Müller et al. |
| 2011/0288160 A1 | 11/2011 | During et al. |
| 2011/0300505 A1 | 12/2011 | Jessop et al. |
| 2012/0126948 A1 | 5/2012 | Brunski |
| 2012/0156637 A1 | 6/2012 | Benz et al. |
| 2012/0219924 A1 | 8/2012 | Walsh et al. |
| 2012/0230017 A1 | 9/2012 | Duffy |
| 2012/0257390 A1 | 10/2012 | Fowler |
| 2012/0269870 A1 | 10/2012 | Jiang et al. |
| 2012/0321736 A1 | 12/2012 | Jaeger et al. |
| 2012/0322026 A1 | 12/2012 | Clark |
| 2013/0034824 A1 | 2/2013 | Wang et al. |
| 2013/0052607 A1* | 2/2013 | Gersh ............. A61C 19/004 433/27 |
| 2013/0117868 A1 | 5/2013 | Cao et al. |
| 2013/0137058 A1 | 5/2013 | Wong et al. |
| 2013/0141934 A1 | 6/2013 | Hartung |
| 2013/0224495 A1 | 8/2013 | Gan et al. |
| 2013/0273493 A1 | 10/2013 | Noui et al. |
| 2013/0344456 A1 | 12/2013 | Jessop |
| 2014/0038125 A1 | 2/2014 | Logan et al. |
| 2014/0051031 A1 | 2/2014 | Kovac et al. |
| 2014/0056951 A1 | 2/2014 | Losick et al. |
| 2014/0057837 A1 | 2/2014 | During et al. |
| 2014/0099596 A1 | 4/2014 | Senn |
| 2014/0161866 A1 | 6/2014 | Cao |
| 2014/0287378 A1 | 9/2014 | Jensen |
| 2015/0062903 A1 | 3/2015 | Hu et al. |
| 2015/0137403 A1 | 5/2015 | Cao et al. |
| 2015/0153027 A1 | 6/2015 | Ma et al. |
| 2015/0202032 A1 | 7/2015 | Benz |
| 2016/0074144 A1 | 3/2016 | Peterson |
| 2016/0113746 A1 | 4/2016 | Bringley |
| 2016/0287364 A1 | 10/2016 | Pauler et al. |
| 2016/0367347 A1 | 12/2016 | Senn et al. |
| 2017/0035539 A1 | 2/2017 | Bringley |

FOREIGN PATENT DOCUMENTS

| | | |
|---|---|---|
| DE | 3 534 342 | 3/1987 |
| DE | 10 2012 212 429 | 1/2014 |
| EP | 1236444 | 9/2002 |
| WO | 96/06521 | 3/1996 |
| WO | 02/080808 | 10/2002 |
| WO | 2009/052016 | 4/2009 |
| WO | 2011/123738 | 10/2011 |
| WO | 2011/139844 | 11/2011 |
| WO | 2013/050587 | 4/2013 |
| WO | 2014/078852 | 5/2014 |
| WO | 2014/135589 | 9/2014 |

(56) References Cited

OTHER PUBLICATIONS

International Search Report and the Written Opinion of the International Searching Authority for International Application No. PCT/US2015/050622 dated Dec. 9, 2015.

* cited by examiner

DENTAL CURING LIGHT

TECHNICAL FIELD

The present disclosure relates to dental curing lights, and more particularly to controlled delivery of light from a dental curing light.

BACKGROUND

With the introduction and subsequent market penetration of light cured composite compounds used for Class 2 restorative dentistry, significant gains were made in the structural quality, natural appearance, and longevity of restorative dental work. However, at the same time, a new curve was thrown at the dentist. Unlike the older traditional amalgam fillings, once a composite filling was successfully placed and shaped, the dentist was still not finished. In an effort to completely polymerize the compound and to try to assure a problem free placement, the dentist would cure the compound with an intense light of a prescribed wavelength. A majority of the early curing lights that were used to achieve this function utilized a halogen based incandescent lamp as the light source. The technology was simple and relatively affordable but it was a bit "power hungry", and produced a high degree of waste heat, both at the lamp and at the tooth being treated. Design refinements to optically filter the wavelengths of the energy that were actually delivered to the tooth significantly reduced the unnecessary heating of the tooth. This was a helpful refinement as the conventional photo activators used to induce cross-polymerization of most restorative compounds only utilize a portion of the blue light spectrum. By filtering out much of the Green, Red, and Infra-Red portions of the light being delivered to the tooth, advancements were made toward eliminating a majority of the unrequired wavelengths that result in nothing more than "waste heat" at the tooth. Typical curing times for a tooth restoration with light cured composites was in the range of 20 to 60 seconds.

Then, in the mid to late 1990s, came the dawn of the blue high brightness LED, and not too long thereafter, the rise of the blue LED curing wand. Blue LEDs that emitted light in the 450 to 485 nanometer wavelength range were well suited, spectrally at least, for the curing of dental composites. Power capabilities and pricing of the new blue LEDs were a limiting factor for several years—well into the new millennia. However, it was not long until LED curing wands providing a reliable 200-300 mW/cm2 (milliwatts per sq. centimeter) were technically viable and commercially available. This allowed introduction of small hand-held battery operated curing lights that could perform 20-60 second composite cure times similar to their older cord based halogen predecessors.

Conventional LED curing wands have advanced significantly beyond the capabilities of the initial blue LED curing wand. There are now hand-held battery operated curing lights capable of producing in excess of 10 times their predecessor's power—many at 3,200 mW/cm2 or more, and some now as high as 8,000 mW/cm2. This results in a curing light that can, in theory, cure a composite placement in a mere 1 to 3 seconds by delivering the target amount of total optical energy (usually measured in Joules) in less than one tenth the time. These advancements, however, are not without downsides.

Some conventional dental light wands operate with means for testing the optical output, such as in the base of the charging stand. However, there is no feedback mechanism incorporated into such a dental light wand, itself.

Conventional LED based curing lights have progressed to address several concerns over the past many years with respect to cordless operation, user ergonomics, digitally controlled exposure times and much higher optical power availabilities. However, these improvements have done little to eliminate many of the causes or issues, such as user variances, that often times prevent safe, repeatable, and reliable compound cures. And, in some respects, the significantly higher power levels of recent curing lights have allowed more frequent over-exposure, which may affect the ability to achieve enhanced safety and repeatable and reliable compound cures.

SUMMARY OF THE DESCRIPTION

An instrument for applying light energy to a light-curable target. The instrument may include a light source capable of outputting the light energy to the target, where the light source is controllable to vary light energy being output. The instrument may include a light sensor for sensing a light energy characteristic, and an optical feedback path operably coupled to the light sensor. The optical feedback path may be disposed to channel light reflected back from the target to the light sensor, where the light sensor is configured to sense a light energy characteristic with respect to the light reflected back from the target. The instrument may further include a controller operably coupled to the light sensor and the light source. The controller may be configured to vary, based on the light energy characteristic sensed by the light sensor, an operating characteristic of the light source to adjust the light energy being output from the light source.

In one embodiment, the optical sensor and related elements form a closed-loop LED curing wand that manages the quantity of delivered energy to a composite restoration at the tooth with much greater precision than conventional curing instruments. The instrument according to one embodiment of the present disclosure does not control the quantity of delivered energy by measuring the amount of light energy created in the LED based wand, but rather by measuring, in real time, the portion of that light that is actually hitting the targeted surface of the tooth restoration at any given moment and then managing the electrical power applied to the LED source within the instrument to drive to desired levels of irradiance at the targeted tooth surface. In so doing, both enhanced quality and enhanced safety of the light cure exposure may be achieved.

In one embodiment, a curing instrument for curing a light-curable material may include at least one of a light source, optical drive circuitry, a controller, an optical feedback sensor, and a light sensor. The light source may be configured to generate light energy to cure the light-curable material, and to provide an illumination beam of light energy to be delivered to the light-curable material. The optical drive circuitry may be configured to provide a power signal to the light source to generate the light energy, where the optical drive circuitry is configured to vary one or more operating characteristics of the power signal to vary the output of light energy from the light source. The controller may be configured to control operation of the optical drive circuitry to control generation of the light energy from the light source, and the optical feedback sensor may be arranged to collect light reflected from the light-curable material. The optical feedback sensor may include a light input with an optical sense path directed to the light-curable material, where the optical sense path of the light input is surrounded by the illumination beam generated from the light source. Optionally, the light input may correspond to a distal end of a fiber-optic element that is constructed according to a side-fire configuration such that the optical sense path is substantially 90° relative to a central axis of the fiber-optic. The distal end may be positioned relative to the illumination beam such that substantial shadowing of the illumination beam is avoided.

The light sensor may be optically coupled to the light input of the optical feedback sensor, and may be configured to generate an optical sensor feedback signal based on the light collected by the light input. Based on the optical sensor feedback signal, the controller of the curing instrument may direct the optical drive circuitry to vary output of light energy from the light source.

A method of manufacture according to one embodiment may include emitting light from the light input of the optical feedback sensor and emitting light from the light source. The method may include comparing the output beam from the light input to the illumination beam of the light source in order to facilitate aligning the output beam with the illumination beam (e.g. coaxial in aligning the output and illumination beams). In embodiments in which the light input is a side fire construction, the optical feedback sensor may be rotated and moved laterally into position such that the output beam is coaxially aligned the illumination beam. After coaxial alignment is achieved, at least a portion of the optical feedback sensor may be affixed to a stationary part of the curing instrument, such as a lens coupled to the light source, to substantially prevent movement of the light input relative to the light source.

In one embodiment, a method of operating a curing light to cure a light-curable material may include at least one of the following steps: generating light energy from a light source, directing that light energy toward a target surface of the light-curable material, generating an optical sensor feedback signal based on sensed light reflected from the target surface, and adjusting output of the light energy from the light source based on the optical sensor feedback signal.

The method of operation may further include one or more of iteratively calculating the amount of light energy applied to the target surface, determining whether the amount of light energy is consistent with a curing operation profile, and determining whether a total amount of light energy directed to the target surface is consistent with a prescribed amount of light energy for curing the light-curable material.

One or more embodiments described herein may achieve a real and effective construction that possibly avoids the potentially dangerous and potentially painful chance of overexposure to light energy, which may lead to thermal tissue damage. In this way, a more powerful curing instrument may be used while avoiding the conventional approach of doubling or tripling exposures. The closed loop LED curing light approach may eliminate the wasted time and at the same time potentially eliminate possibly adverse effects associated high power curing lights.

These and other objects, advantages, and features of the disclosure will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION

Figure 1:
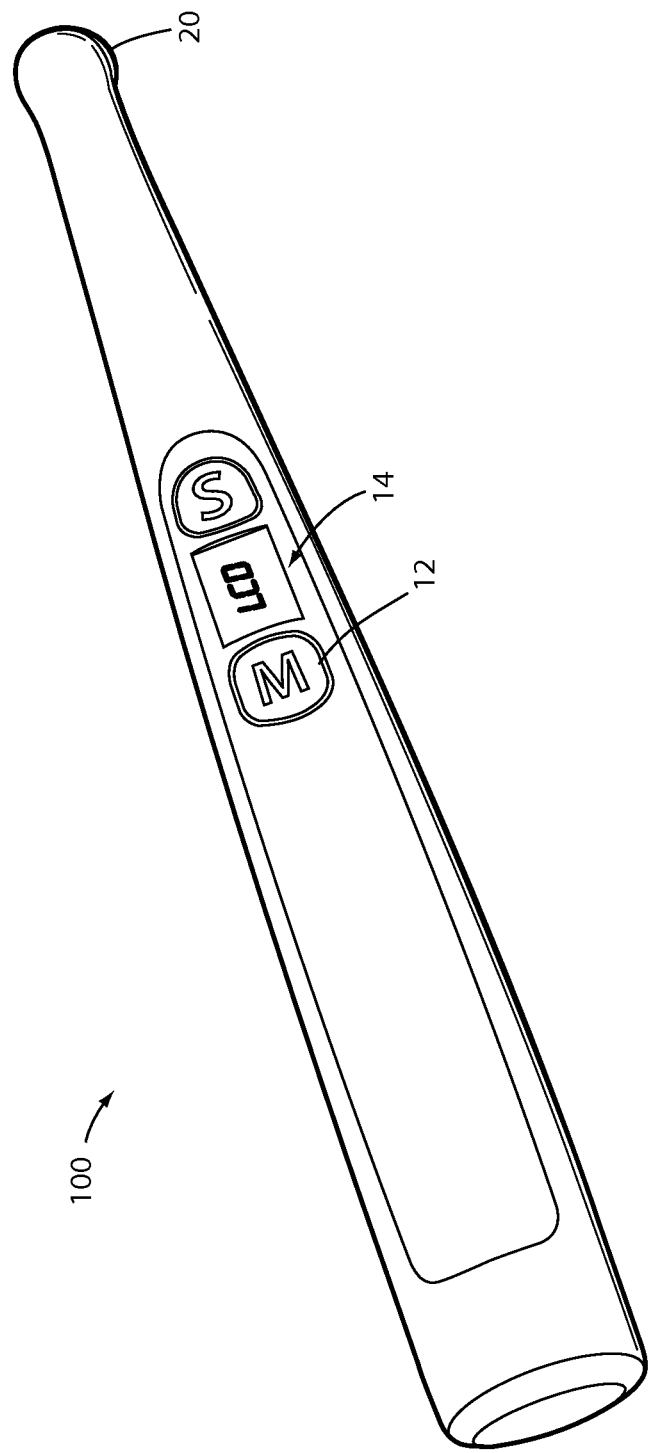
FIG. 1 depicts a curing instrument according to one embodiment.
Figure 2:
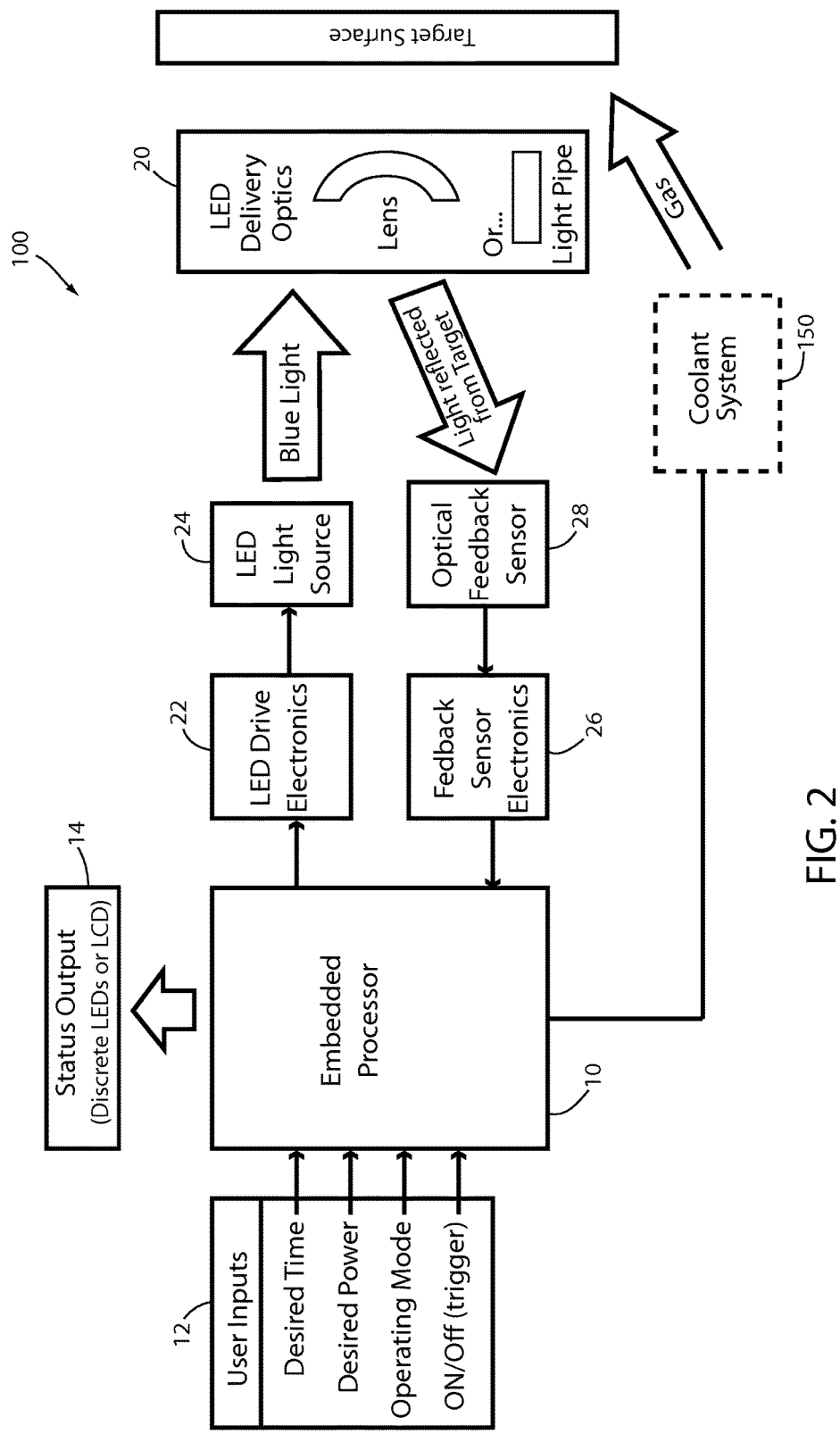
FIG. 2 shows a representative view of the dental curing instrument of FIG. 1.

A curing instrument for providing light to a composite material during a cure is shown in FIGS. 1-2 and generally designated 100. The curing instrument 100 may be used to cure a light activated composite material, such as by polymerizing monomers into durable polymers. The curing instrument 100 may be a standalone device, such as a portable handheld wand having a battery power source, or a component of a curing system having a base unit to which the curing instrument 100 is tethered and receives power therefrom. A variety of fields may benefit from the curing instrument 100, including, for example, the dental and medical fields. For purposes of disclosure, the curing instrument 100 is described as being a dental curing instrument for use in connection with curing a composite material having photo initiator, which absorbs light of a particular wavelength and causes polymerization of the monomers included in the composite material into polymers. It should be understood, however, that the present disclosure is not limited to the curing instrument being a dental curing instrument or limited to use with dental composite material—any curing application may benefit from the curing instrument, and any type of photo curable material may be used in conjunction with the curing instrument, including transparent, translucent and opaque curable materials.

In the illustrated embodiment of FIGS. 1-2, the curing instrument 100 may include a light application member 20, an operator interface 12 and an operator feedback element 14. In use, an operator may activate the curing instrument 100 via the operator interface 12 (e.g. a start button "S") to initiate a curing operation of a composite material (not shown). After activation, the curing instrument 100 may generate and emit light through a light passage of the application member 20. The operator may position the light application member 20 such that the light passage directs light toward the composite material in order to effect a cure thereof.

The operator interface 12 may enable operator selection of one or more settings or modes of the curing instrument 100, as described herein, such as by selecting a input (e.g., a mode button "M"). For example, the operator interface 12 may enable operator selection of one or more of a desired curing or exposure time, a desired power output, an operating or delivery mode, and an ON/OFF trigger. The one or more settings or mode selector by the operator may be identified via the operator feedback element 14, which may include one or more LEDs or a display, or a combination thereof. With the operator feedback element 14, the operator may be informed or made aware of operational settings or modes of the curing instrument 100. In one embodiment, the operator feedback element 14 may include a display in the form of an LCD or LED display.

The curing instrument 100 may be configured to control emission of light from a light source based on feedback from an optical sensor. In some cases, output from the light source may be tightly managed to account for variations in battery charge, LED life, and other related system component variations, or a combination thereof, in an effort to achieve consistent generation of light or power output from the light source. However, even with such management, deviations may occur in delivery of a desired light level or power output at the intended target (e.g., the composite material). Many factors "external" to the curing instrument 100 may affect light delivery, including a variety of operator errors such as contamination of a tip or light output of the curing instrument 100, or distance and angular variations between the light output of the curing instrument 100 and the targeted surface (e.g., a tooth surface) during the cure. These and other external factors may significantly impact how much optical energy actually makes it to the intended or targeted surface. The curing instrument 100 may be configured to utilize optical feedback to adjust light output in order to substantially reduce or eliminate the effects of external error sources, which can often be the principal factor or factors in how much optical energy makes it to the targeted surface.

The curing instrument 100 according to one embodiment may sense one or more characteristics indicative of the amount of light actually making it to the targeted surface, which includes the composite material, such as a compound restoration that is targeted for curing. Based on the one or more parameters, the curing instrument 100 may "throttle" the light source output, either up or down, to achieve a target irradiance power (mW/cm2) and total energy (Joules/cm2) delivered to the targeted surface.

In other words, the curing instrument 100 may be configured to control an amount of total optical energy applied (Joules) to the intended target, and in so doing, the rate of power applied to the target (mW/cm2) during the exposure time may be controlled to avoid exceeding a target level of optical energy. Control over optical energy output based on optical feedback can be achieved in a variety ways. For purposes of disclosure, the present disclosure includes several embodiments that implement such control-based delivery of light to a curable material. However, it should be understood that the present disclosure is not limited to the specific constructions and embodiments described herein, and that essentially any controlled curing instrument is contemplated.

In the illustrated embodiment of FIG. 2, the curing instrument 100 may include a controller 10 (e.g., a low end embedded controller), optical drive circuitry 22, a light source 24, optical feedback circuitry 26, and an optical feedback sensor 28. The optical drive circuitry 22 may control the supply of power to the light source 24 to generate light that may be transmitted via the light application member 20 to a target surface. For instance, the optical drive circuitry 22 may include controlled drive circuitry that receives power from a power source (e.g., a battery of the curing instrument 100), and provides that power as a power signal to the light source 24 according to one or more operating characteristics, such as a voltage magnitude or current magnitude, or both. In response to receipt of power, the light source 24 may generate light that can be directed to a target surface for the curing operation. The light source 24 in the illustrated embodiment is primarily an Ultra-Violet (UV) light source, such as a UV light emitting diode (LED), but may be configured differently, including being configured to primarily output infrared light. It should further be understood that the light source 24 of the illustrated embodiment—although primarily one type of light source (e.g., UV)—also may emit light of wavelengths different from those of the primary light type. For instance, the primary light output from a UV LED is UV light, but the UV LED may also emit light in the visible spectrum or infrared spectrum, or both, along with the UV light.

The controller 10 of the curing instrument 100 in one embodiment may include an algorithmic computational solution element or controller module, such as a shared computational module incorporated into the controller 10, forming an embedded control system that controls light output and potentially additional instrument functionality. Optionally, this module may be separate from the controller 10 and incorporated into another hardware module that along with the controller 10 forms at least part of a control system for the curing instrument 100.

Control over generation of light from the light source 24, as mentioned herein, may be conducted through the optical drive circuitry 22, which is also referred to as an LED power control element but is not so limited. In the illustrated embodiment, the controller 10 may be coupled to and control operation of the optical drive circuitry 22. The controlled level of the operating characteristic or operating characteristics of the optical drive circuitry 22 may be governed at least in part by the controller 10 to affect the power signal provide to the light source and to affect light output thereof. For example, the controller 10 may provide a control signal or control information to the optical drive circuitry 22 to provide power to the light source 24 according to a target operating characteristic. The control signal or control information provided from the controller 10 may be dynamic such that, during a curing operation, the control signal or control information may vary to effect a change in the target operating characteristic. The optical drive circuitry 22, in one embodiment, may utilize feedback circuitry to achieve the target operating characteristic. For instance, the optical drive circuitry 22 may include a current sensor that senses current supplied to the light source 24, and based on the sensed current, the optical drive circuitry 22 may adjust operation to vary the supply current to more closely align with a target supply current. Additionally or alternatively, the controller 10 may direct operation of the optical drive circuitry 22 based on sensed information related to operation of the optical drive circuitry 22 in supplying power to the light source 24, including, for example, adjusting one or more target operating characteristics, such as duty cycle, based on a deviation between a target current and a sensed operating current.

The optical drive circuitry 22 may include circuitry that turns ON/OFF the light source 24, and that manages the power output during use. The optical drive circuitry 22 may receive input from the controller 10 to control the output of the light source 24. The optical drive circuitry 22 may include the capability of managing output power of the light source 24 with more resolution that merely turning ON or OFF or selecting one of two or three preset power levels. For instance, the optical drive circuit 22 may control one or more operating characteristics, including, for example, controlling duty cycle of power applied to the light source 24 to control the amount of output power. As another example, the optical drive circuitry 22 may control the amplitude or the rail voltage, or both, of power applied to the light source 24 to affect and control output power. In some circumstances, the optical drive circuitry 22 may be controlled by the controller 10 to achieve "ramping" exposure profiles, or exposure profiles or operating profiles that change over the course of the curing operation rather than a profile configured to supply a substantially constant amount of light energy to a target surface. For instance, the curing instrument 100 may vary an output level of the light source 24 to achieve controlled supply of light energy to a target surface—with adaptive exposure profiles, a target output level of the light source 24 may be shifted or varied over the course of the curing operation while the controller 10 controls supply of power to the light source 24 according to the target output level for a given time of the curing profile in the curing operation. As an example, the curing instrument 100 may supply a greater amount of light energy to a target surface for a beginning period of the curing operation, and supply a lesser amount of light energy during later period of the curing operation.

The controller 10 of the curing instrument 100 may control the optical drive circuitry 22 based on feedback obtained from an optical feedback sensor 28. Such optical feedback-based control may be implemented in conjunction with any of the control methodologies described herein, including, for example, controlling one or more operating characteristics based on feedback from the optical feedback sensor 28 to achieve a target optical output. In the illustrated embodiment of FIG. 2, the curing instrument 100 may include an optical feedback sensor 28 configured to sense light reflecting from the target surface, to which light from the light source 24 is directed, and including an optical feedback path configured to channel light or a characteristic of light to optical feedback circuitry 26. Based on optical feedback from the optical feedback sensor 28, the optical feedback circuitry 26 may generate an optical sensor feedback signal indicative of the sensed light and provide the optical sensor feedback signal to the controller 10. By analyzing the optical sensor feedback signal, the controller 10 may dynamically vary the control signal or control instructions provided to the optical drive circuitry 22, thereby dynamically adjusting one or more operating characteristics of the optical drive circuitry 22 and output from the light source 24 based on sensed light reflected from the target surface. Additionally, or alternatively, the controller 10 may determine one or more timing aspects related to delivery of light based on the optical sensor feedback signal, and dynamically calculate a duration for applying light to the targeted surface. For instance, based on the optical sensor feedback signal, the controller 10 may determine an amount of light energy delivered to the target surface or a given amount of time, and instruct or command the optical drive circuitry 22 to discontinue delivering light energy in response to the amount of delivered light energy reaching or exceeding a threshold.

The curing instrument 100 according to the illustrated embodiment may include a light sensor element in the optical feedback circuitry 26 that is receives light or a characteristic thereof via the optical feedback path of the optical feedback sensor 28. The light sensor element of the curing instrument 100 may be located so as to be systematically connected to the controller 10 so that output of light from the light source 24 may be controlled based on sensed light. The light sensor element of the optical feedback circuitry 26 may be a photodiode that is sensitized to one or more wavelengths of light, such as the spectrum of light corresponding to UV radiation. It should be understood that any type of light sensor element may be incorporated the optical feedback circuit 26, and that the light sensor element may be sensitive to more than one spectrum of light. The optical sensor feedback signal received by the controller 10 may be an analog signal from the optical feedback circuitry 26. The controller 10 may be configured to convert the analog signal to digital information for further processing as described herein. Additionally, or alternatively, the optical sensor feedback signal provided by the optical feedback circuitry 26 may be a digital signal representative of information or data relating to reflected light sensed by the light sensor element of the optical feedback circuitry 26.

As an alternative or in addition to the light sensor element, the curing instrument 100 may utilize a light and/or heat sensor that is located at or substantially near the targeted surface of the tooth. This configuration may offer enhanced accuracy for controlled delivery of energy to the tooth. This configuration may also be usable with less calibration.

In one embodiment of the curing instrument 100, the optical feedback sensor 28 may serve to preferentially collect some portion of the light reflected off from the surface of the intended target area of the area (e.g., the composite material) being treated, and may also serve to deliver this light to the light sensor element of the optical feedback circuitry 26 for quantification. The optical feedback sensor 28 may be positioned relative to the light application member 20 such that a light input 58 of the optical feedback sensor 28 is disposed to collect light reflected from the target surface. The optical feedback sensor 28 according one embodiment may be an optical fiber with the light input 58 being formed at a distal end of the optical fiber. The light input 58 may be surface treated, such as by polishing, so that the light input 58 is configured to collect reflected light, as described herein. In one embodiment, the optical fiber may be configured such that a distal end corresponding to the light input 58 is constructed as a side-firing tip. With this construction, the optical fiber may collect light at an angle different from a central axis of the optical fiber, including, for example, light directed substantially perpendicular with respect to a central axis of the optical fiber. The distal end of the optical fiber in a side fire configuration may be treated such that a surface of the distal end is angled (e.g., about 42 deg.) relative to the central axis of the optical fiber. It should be understood that the optical feedback circuit 28 may be arranged to collect light at different angles, including, for example, between 20 and 160 deg. relative to the central axis of the optical fiber.

In the illustrated embodiment, the light sensor 28 may not be configured for the purpose of sensing LED output from the light source 24, but rather to sense the light reflected back from the targeted surface. This light sensor arrangement may achieve an optical connection between the optical feedback circuitry 26 and the "target" surface via the optical path element or light sensor 28. Such an optical path may be accomplished by an isolated, dedicated optical fiber, or by other blended optical arrangements, so as to enable the optical signal received by the light sensor of the optical feedback circuitry to largely, or at least in part, include the light reflected off of the targeted surface. The optical sensor feedback signal, generated by the optical feedback circuitry 26 and based on the light provided via the optical path of the light sensor 28, may then be processed by the controller 10 to eliminate or greatly reduce known and derived sensory error sources as well as to compensate for optical factors impacting the optical sensor feedback signal and to thereby compute in real-time a "delivered" energy level (in mW/cm2) at the actual targeted surface. As explained herein, the computation of actual irradiance level at the targeted surface may form a basis of operation according to one or more methods or modes of operation.

In one embodiment, the controller 10 may be configured to control the output of light from the light source 24 based on the optical sensor feedback signal according to a first operational mode in which the real-time "delivered" energy value may be digitally integrated during the time of the exposure to compute the total Joules of energy delivered to the targeted surface up to that point. As the delivered energy reaches the desired level (for example, 48 Joules for a dark shade restoration) the controller 10 of the curing instrument 100 may automatically turn off the light source 24 and notify the operator that the exposure has been completed. In a second operational mode, the curing instrument 100 may use the computed irradiance at the targeted surface (e.g., the tooth or composite material surface) to create an "error value" in real time that represents the over or under exposure at the targeted surface for that moment in time with respect to a target irradiance level initially set or expected by the operator of the curing instrument 100. This error signal may be used as a basis for throttling the light source 24 up or down to substantially ensure that the target surface is receiving a desired amount of mW/cm2 of irradiance at any given moment of the curing process or operation. This second mode may also help to ensure that overly intense irradiation levels are avoided instead of merely shortening the total exposure time.

Figure 3:
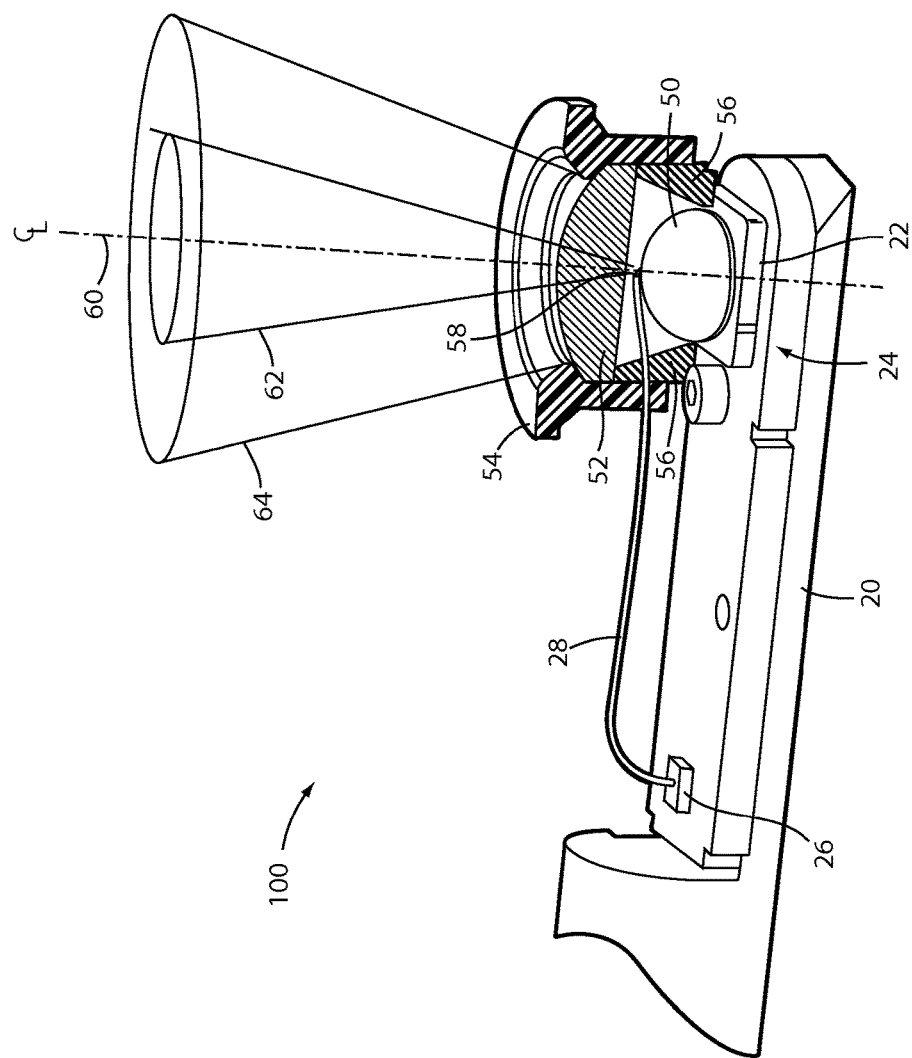
FIG. 3 shows a partially sectioned and exposed view of a light application member of the dental curing instrument of FIG. 1

A partially exposed and partial sectional view of the light application member 20 according to one embodiment of the curing light 100 is depicted in the illustrated embodiment of FIG. 3. The light application member 20 may include the optical drive circuitry 22, the light source 24, the optical feedback circuitry 26, and the optical feedback sensor 28. The light application number 20 may also include a hemispherical lens 50 mounted to the light source 26, a plano-convex lens 52 configured to direct light energy from the light source 24 to a target surface and a reflector ring 56 configured to direct light toward the plano-convex lens 52. The light application member 20 may also include a bezel or outer retainer ring 54 constructed to maintain the position of the plano-convex lens 52, the light source 24, and the reflector ring 56. It should be understood that one or more of the lens types and lens construction of the light application member 20, as well as the physical arrangement or use of one or more components including the bezel 54 and the reflector ring 56, may be different and may vary from application to application.

In the illustrated embodiment, the light source 24 and the light input 58 of the optical feedback sensor 28 may be disposed such that an optical path 62 of the light input 58 is within an optical path 64 of the light source 24. For instance, the optical path 62 of the light input 58 may be coaxial and narrower with respect to the optical path of the light source 24. In operation, the optical path 62 of the light input 58 may be arranged to collect light to sense as a basis for controlling operation of the curing instrument 100, whereas the optical path 64 of the light source 24 may be arranged to direct light from the light source 24 to a target surface. The optical path 62 may be considered part of the optical feedback path provided by the optical feedback sensor 28 to channel light to the light sensor of the optical feedback circuitry 26.

At manufacture, as discussed herein, the optical feedback sensor 28 may be energized from a light source to emit light from the light input 58, thereby facilitating alignment of the optical path 62 of the light input 58 with respect to the optical path 64 of the light source 24. For instance, by emitting one type of light from the light input 58, a comparison can be made against another type of light emitted from the light source 24 in order to align the optical path 62 of the light input 58 with respect to the optical path 64 of the light source 24. After alignment has been conducted, the optical feedback sensor 28 may be secured in place, such as by utilizing optical glue to affix a portion of the optical feedback sensor 28 to a portion of the light application number 20, to substantially prevent linear and rotational movement of the light input 58 of the optical feedback sensor 28.

By aligning the optical path 62 of the light input 58 with respect to the optical path 64 of the light source 24, the curing light 100 may achieve enhanced accuracy in the optical sensor feedback signal used by the controller 10 to provide the closed loop control of the curing light 100.

In the illustrated embodiment of FIG. 3, the light input 58 of the optical feedback sensor 28 may be disposed to capture the light reflected from the target surface, and such that the optical path 62 is aligned with and coaxial about a central axis 60 of the optical path 64 of the illuminating beam of the light source 24. In this way, the optical path 62 of the light input 58 may be considered a sensing optical path, and the optical path 64 of the light source 24 may be considered an illuminating optical path. Alignment of the illuminating and sensing optical path, such as coaxial alignment of these optical paths, may assure that the sensed zone of the target surface does not substantially migrate within the illuminated zone of the target surface as a function of distance from the source. In other words, if the pair of illuminated and sensed optical paths (or "beams") 64, 62 have different trajectories, the sensed zone of the sensing optical path 62 may move substantially outside the illuminated zone of the target surface as the distance between the light application member 20 and the target surface increases. By aligning the sensing beam or "viewed area" of the target surface with the illumination beam, the illumination beam can be convergent, divergent, or even highly collimated, or a combination thereof, without significantly affecting the feedback signal generated from the sensing beam.

Alignment of the illumination optical path 64 and the sensing optical path 64, including coaxial alignment, with respect to the target surface may help to assure that the optical sensor feedback signal is stable over varying distances. Distance is one of the principal variables introduced into a curing operation during handheld operator use. Stabilization of the optical sensor feedback signal over varying distances may enable the curing light 100 to compensate for operator introduced variations in distance, enabling more accurate delivery of light during a curing operation.

Alignment of the optical path 62 of the light input 58 and the optical path 64 of the light source 24 may be achieved in a variety of ways, as discussed herein. In one embodiment, this alignment may be achieved by utilizing a beam splitter technique, including, for example, directing light from the light source through a 45 deg. beam splitter so that part of this light is directed to a first side and the other part of this light is directed to the target surface. Light reflected from the target surface may interface with the beam splitter such that some of the reflected light passes through toward the light source, and the other part of the reflected light is directed to a second side, which is opposite the first side. A sensor may be optically coupled to the second side to detect a characteristic of the reflected light, which can be used as a basis for closed loop feedback control of the light source.

In the illustrated embodiment, the optical path 62 of the light input 58 may be aligned with the optical path of the light source 24 through management of the physical size of the light input 58 and the optical feedback sensor 28, enabling collection of light via the optical path 62 where the light input 58 is substantially small relative to an intersecting surface area of the optical path 64 or the illumination beam. In other words, the optical feedback sensor 28, including the light input 58, may be constructed and positioned such that the amount of area of the optical path 64 that is covered by the optical feedback sensor 28 is small in relation to the total area of the optical path 64 in the same plane as the covered area. In this way, a shadowing effect of the optical feedback sensor 28 may be reduced, or put differently, the optical feedback sensor 28 may be constructed and positioned so that it does not provide a measurable or significant impact on the uniformity or intensity of the illumination beam on the target surface. As an example, the optical feedback sensor 28, as described herein, may be a "side-fire" type of optical fiber in which the light input 58 corresponds to a distal end that is terminated and polished to achieve a near right angle distribution cone or reception cone, or both, at the light input 58. A small optical fiber may be utilized, e.g., within range of 0.005" to 0.020" in diameter, such as 0.010" in diameter, with a side-fire optical termination (as provided, for example, by Polymicro Fibers), and placed into the illumination path close to the light source 24 with a coaxial alignment to avoid significant shadowing. This construction may achieve a useful alignment of the optical path 62 and optical path 64 in a cost-effective manner without substantially adversely affecting curing of the target surface with the light source 24.

The curing instrument 100 according to one embodiment may be a high power (>2000 mW/cm2) LED based dental curing wand. More specifically, the curing instrument 100 may be capable of varying an optical output level of the light source 24, such as a high power LED, to cure a dental composite material according to manufacturer specifications for the material. The curing instrument 100 may form part of an optical delivery system that according to one embodiment may be capable of sustaining at least 2000 mW/cm2 at a target distance of 2 cm to 5 cm from the a tip of the light application number 20, and may be configured such that a profile of irradiance across the beam generated by the tip is substantially homogeneous within 20% of the average power across the tip. It should be understood that the present disclosure is not limited to these features and that alternative instrument or wand configurations are contemplated.

A curing instrument 100 according to one embodiment with all or some of the features described above may achieve closed-loop control of light output to a target surface. Alternatively or additionally as another mode of operation, the curing instrument 100 may achieve open loop control of light output to the target surface. With the ability to sense optical output as feedback, and to use the feedback to compute, track, and compensate for actual optical energy being delivered to the surface of the tooth, the curing instrument 100 may significantly enhance clinical performance and provide enhanced safety in curing dental restorative compounds. In so doing, the curing instrument 100 may help to substantially eliminate a great number of variables impacting exposure level at the targeted surface and the subsequent post-procedural problems that sometimes occur with either under exposure (e.g., insufficient cure of compound) or over exposure, which may potentially cause damage to live tissue from over-heating.

A curing instrument 100 according to one embodiment may be configured with a quality optical design by implementing controlled manufacturing processes to produce an instrument that demonstrates a substantially homogeneous field of light across the tip of the instrument that is consistent from use to use, even if the light source 24, itself, is inclined to exhibit a slight, but continuous, decay in its output level over its "life". It is noted that LEDs often times do not "burn out" in a catastrophic fashion as do their incandescent counterparts, but rather tend to slowly decrease in intensity over their life. LED lifetime can be expressed as the number of hours before they reach either 50% or 70% of original intensity, depending on the LED "life" standard that is being used. The controller 10 of the curing instrument 100 may adjust output intensity of the light source 24 based on the optical sensor feedback signal to counteract degradation of the light source 24 over its lifetime. The controller 10 may also conduct diagnostic analysis based on the optical sensor feedback signal, such as determining whether the light source 24 is operating according to one or more operational parameters sufficient for conducting a cure operation. In this way, the controller 10 of the curing instrument 100 may conduct built in diagnostics (BIT). Additionally, or alternatively, the BIT conducted by the controller 10 may include analysis of battery or power source stability or sufficiency or both, and determining whether contamination is present on a lens or tip through which light is emitted from the light application member 20.

After light from the light source 24 reaches the tip of the instrument, many additional variables can, and sometimes do, impact the effective delivery of those photons onto the intended surface. In cases of hand held use by an operator, probably the most significant of these variables is the operator's accuracy (or variance) with respect to placement of the curing instrument 100 during the time of the exposure or the curing operation. Depending on various factors, such as the optical design of the tip of the light applicator member 20, its effective numerical aperture, and the geometry of tip diameter vs. intended working distance, a variation of better than 5 to 1 can be experienced in light attenuation during hand held curing operations. As an example, clinically relevant irradiance has been demonstrated to drop off significantly in some cases due to a change in target distance from 2 mm to 8 mm. Furthermore, additional variation as high as 2 to 1 may occur from angular variation between the axis of the tip surface and the normal of the target surface being treated. The curing instrument 100 according to one embodiment may be configured to substantially account for this variability by utilizing closed loop feedback based on sensed light reflected from the target surface, thereby enabling control over the irradiance.

It should be understood that the curing instrument 100 according to one embodiment may implement closed loop control of light output based on a sensed parameter or characteristic of light reflecting from the target surface, which itself may be indicative of the light energy at or reaching the target. In addition to basing control on the light sensed at the target, the instrument may internally sense internal light output from the light source 24 of the curing instrument 100. Internally sensing the light output, alone without determining the amount of light externally applied to the target, may allow the curing instrument 100 to compensate for aging or variations in the light source or lamp, but generally does not account for variables that may exist between the source generation of the curing instrument 100 and the intended final target destination of the light. Operator variations from use to use may be compensated for by sensing a parameter indicative of the light actually reaching the target.

The acceptance and utilization of composites for dental restoration has grown tremendously over the last couple of decades, including use of composites on anterior teeth. Use of anterior tooth composites has given rise to composites of different shades to match the same color of the natural tooth to which the composite is being applied. The different shade offerings, in many cases, call for different amounts of target light energy to complete a cure. Darker shades often cause much more internal attenuation of light as it is scattered about and transmitted through the composite material. This often results in increased target energy to cure the darker shades. As an example, a popular line of restorative compound offered by Dentsply cures at about an energy of 6 Joules/cm$^2$ for lighter shades, but cures at 48 Joules/cm$^2$ for darker shades. This is an eight-to-one variation in prescribed energy delivery and as such represents an additional 8 fold increase in the total range of appropriate energy levels that may now be prescribed to achieve a target cure for various composite materials.

The curing instrument 100 according to one embodiment may be configured to cure a restorative compound by controlling light output during the cure cycle to achieve a target output, possibly specific to the curable material or restorative compound being used. For instance, the operator may utilize the operator interface 12 to select a target cure setting for a curing operation that is prescribed by a manufacturer of the curable material being used. In this way, the amount of light energy applied during a curing operation may be selectively chosen based the material being used rather than "over-curing" the curable material by a factor of two or three to eliminate a potential under-cure due to distance, angle, or other external variation factors. If curing intensity levels are considered low (e.g., 200 to 300 mW/cm2), intentional over-curing a curable material by a factor of two or three to eliminate a potential under-cure due to distance, angle, or other external variation factors is often not considered to be an issue. However, with use of curable materials that prescribe higher cure energies, and therefore a higher energy curing instrument (e.g., an instrument that produces at least 1200 mW/cm2 and possibly up to 3000 mW/cm2 or more), intentional over-curing can result in application of energy that is an order of magnitude greater than that of direct sunlight (e.g., 100 mW/cm$^2$). The curing instrument in the illustrated embodiment of FIG. 2 may utilize optical feedback based on light reflected from the target surface to control the delivery of light energy, thereby substantially avoiding significant over-curing and intentional over-curing procedures that generate light energies two to three times the prescribed amount.

Figure 4:
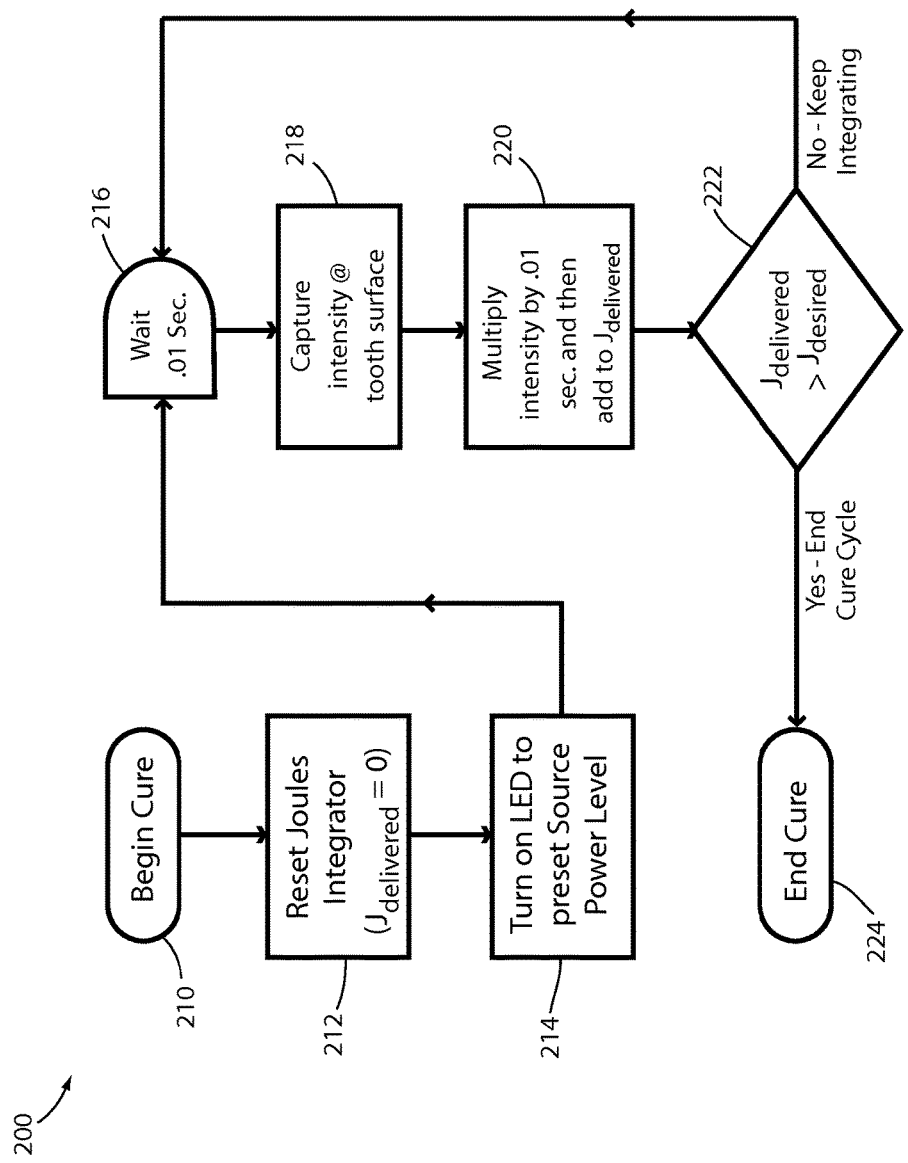
FIG. 4 is a method of operating a curing instrument according to one embodiment.

A method of operation of the curing instrument or curing system according to one embodiment is depicted in the illustrated embodiment of FIG. 4, and generally designated 200. The method 200 may be implemented as a control module in the controller 10 using feedback based on one or more parameters or characteristics, such as reflected light from the target surface, and one or more sense characteristics of the curing instrument 100, itself. In the illustrated embodiment, the method 200 may include initiating a cure operation and resetting an accumulator or integrator that tracks an amount of light energy delivered to a target surface. Steps 210 and 212. The controller 10 may then instruct the optical drive circuitry 22 to power the light source 24 according to an initial setting, such as a preselected source power level, thereby starting application of light to the targeted surface. Step 214. The real-time "delivered" energy value may be digitally integrated during the time of the exposure to computationally represent the total Joules of energy delivered to the targeted surface up to a given point in time. Steps 216, 218. As the delivered energy reaches the desired level (for example, 48 Joules for a dark shade) the controller 10 may automatically turn off the light source 24 and notify the user that the exposure has been completed. Steps 220, 222, 224. In this way, the curing instrument 100 may vary the exposure time to compensate for factors affecting delivery of light energy to the target surface, such as distance or angular variations present during each use.

Figure 5:
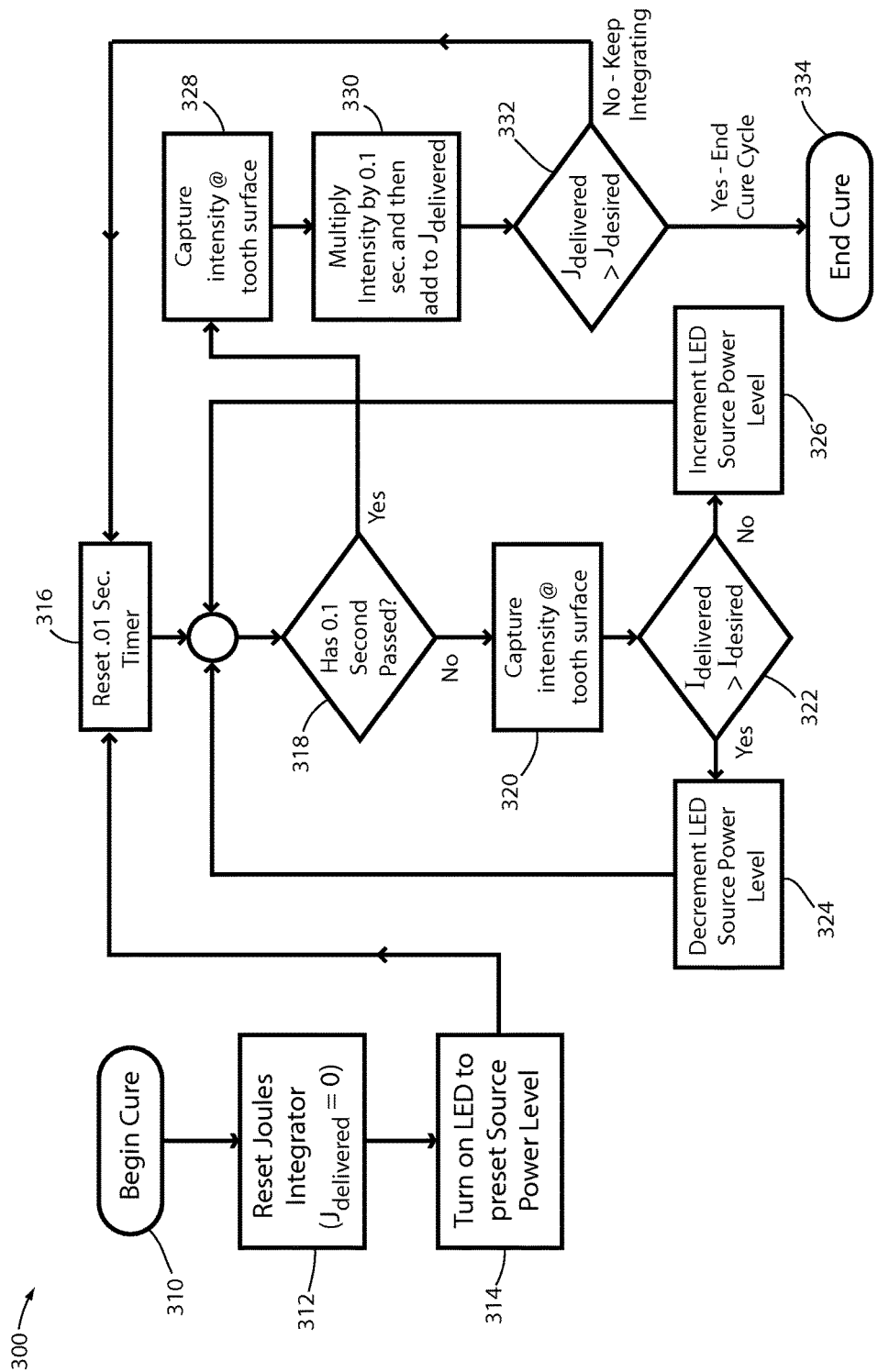
FIG. 5 is a method of operating a curing instrument according to one embodiment.

Another method of operating the curing instrument according to one embodiment is depicted in the illustrated embodiment of FIG. 5, and generally designated 300. The method 300 may be implemented by a controller 10 similar to the method 200. In the illustrated embodiment, the method 300 may include initiating a cure operation and initializing or resetting an accumulator or integrator that tracks an amount of light energy delivered to a target surface. Steps 310 and 312. Initiation of a curing operation may start in response to activation of a user input (e.g., a button) of the operator input 12. The controller 10 may then instruct the optical drive circuitry 22 to power the light source 24 according to an initial setting, such as a preselected source power level, thereby starting application of light to the targeted surface. Step 314. The method 300 may further include computing irradiance at the targeted surface to generate an error value in real-time that represents the over or under exposure at the targeted surface for that moment in time with respect to a target irradiance level initially set or expected by the operator. Steps 318, 320.

This error signal may then be used as a basis for adjusting the optical drive circuitry 22 so as to either increase or reduce output from the light source 24 by a calculated value and thereby assure that energy losses between the light source 24 and the target surface are compensated and that the target surface is receiving the target number of mW/cm2 of irradiance at any given moment of the curing process. Steps 322, 324, 326. As an example, at step 322, the method 300 may determine whether the amount of irradiance delivered ($I_{delivered}$) is greater or less than a calculated amount of expected irradiance, which may correspond to the desired or expected amount of irradiance ($I_{desired}$) for a given time. As another example, the method 300 may determine whether the amount of energy delivered ($J_{delivered}$) is greater or less than a calculated amount of expected energy, which may correspond to the desired or expected amount of energy ($J_{desired}$) for a given time period, or correspond to a fraction of the total prescribed amount of energy for the curing operation for the period of time since the curing operation was initiated. The method 300 may facilitate substantial avoidance of overly intense irradiation levels instead of shortening the total exposure time.

The method 300 of the illustrated embodiment may after a predetermined amount of time, such as 0.01 s, determine, based on the optical sensor feedback signal, whether the total amount of energy delivered to the target surface meets or exceeds a threshold corresponding to a prescribed amount of light energy for a curing operation. Steps 328, 330, 332. If the calculated amount of total energy satisfies this condition, the curing operation may be terminated. Steps 332, 334. If the condition is not met, the curing operation may continue such that the calculated amount of energy is determined iteratively until the calculated amount of total energy satisfies the condition. Steps 332, 316.

The curing instrument 100 according to one embodiment may provide a construction that substantially ensures curable materials, such as composite dental materials, receive sufficient energy to properly cure the curable material without relying on a conventional and much less accurate approach of simply doubling or tripling a calculated exposure time. In this way, a substantially effective energy deliverance to the target surface may be achieved. It should be understood that the techniques and embodiments described herein may be extended to non-dental applications such as industrial manufacturing where precise light cure of adhesives or similar composite fills are utilized.

Optionally, the curing instrument 100 may be configured to least one of prevent operation or alert the operator of issues related to improper alignment or an insufficient capability to deliver energy, such as in case a curing operation appears, based on the optical sensor feedback signal, to be insufficient to properly cure the curable material. As an example, if the curing instrument 100 is improperly angled, possibly due in part to an improperly trained operator, the controller 10 may detect that the curing operation is insufficient to cure the target material, and alert the operator accordingly, or discontinue operation, or both.

Figure 6:
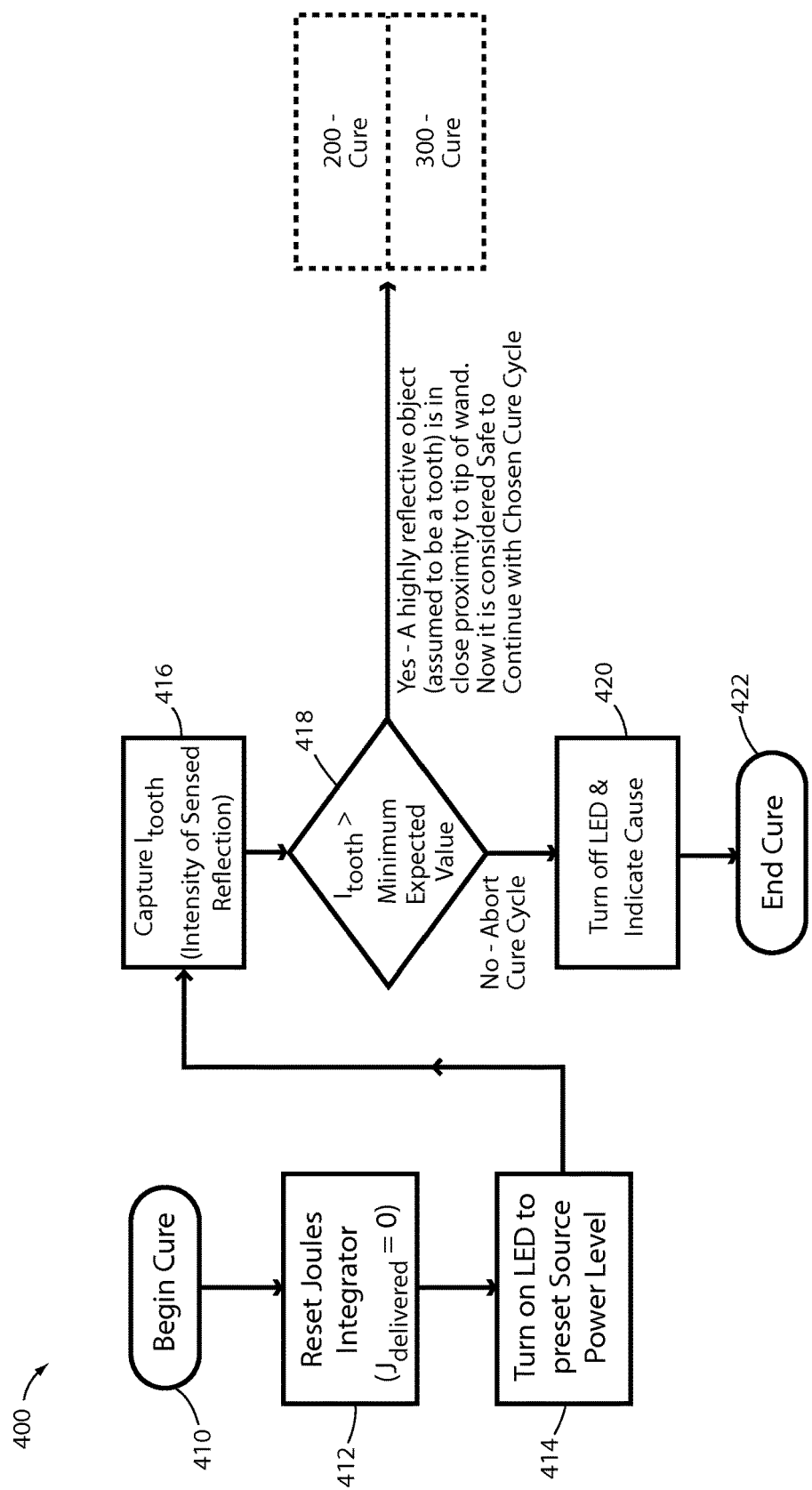
FIG. 6 is a method of operating a curing instrument according to one embodiment.

A method of the curing instrument or curing system according to one embodiment is depicted in the illustrated embodiment of FIG. 6, and generally designated 400. In the illustrated embodiment, the method 400 may be conducted prior to conducting a curing operation according to one or more of the methods described herein, such as the methods 200, 300. The method 400 may include, in response to activation of a user input of the operator input 12 (e.g., a button), resetting or initializing an accumulator or integrator of sensed energy delivered to a target surface. Steps 410 and 412. The controller 10 may then instruct the optical drive circuitry 22 to power the light source 24 according to an initial setting, such as a preselected source power level, thereby starting application of light. Step 414. The controller 10 may analyze the optical sensor feedback signal provided from the optical feedback circuitry 26 to determine if the sensed reflected light is indicative of the curable material actually being targeted by the light application number 20. Steps 416, 418. As an example, the controller 10 may compare the sensed light to a threshold, parameter, or parameter range associated with the type of curable material being targeted to determine whether the curable material is actually receiving light from the light source 24. If the sensed light is less than the threshold, or deviates from the parameter range, the controller 10 may determine the curable material is improperly positioned relative to the light application number 20 such that a curing operation is unlikely to be effective. Based on this determination, the controller 10 may discontinue operation of the light source 24 or alert the operator of an issue via the operator feedback circuitry 14, or a combination thereof. Step 420, 422. If the sensed light satisfies one or more criteria, such as being greater than a threshold, indicative of proper targeting of the curable material, the controller 10 may proceed with further steps in the curing operation, including one or more steps described herein in connection with the methods 200, 300. The method 400 may transpire over the course of several microseconds to substantially avoid application of light energy to surfaces other than that of a known or desired type of target.

In an addition to or as an alternative to one or more embodiments described herein, the curing light 100 may include an air path to conduct air or another gas toward or away from the target surface, thereby cooling the target surface or the surrounding area, or both. As an example, as shown in broken lines in FIG. 2, the curing light 100 may include a coolant system 150, including, for example, a pressurized air or vacuum source and an air path to conduct air from or to the target surface. In this way, air or another gas may be pushed or pulled, respectively via pressure or vacuum, past the target surface being cured to induce accelerated surface cooling at the target surface by virtue of increased air flow. The coolant system 150 may also utilize other cooling mechanism besides gas flow, such as directing water vapor or water mist toward the target surface.

In one embodiment, the coolant system 150 may include a coupler, possibly disposed at or near a base of the curing instrument 100, that allows a quick and reliable connection to a source of the pressurized gas or vacuum. The coolant system may include an air channel located within the body of the curing instrument to direct and contain the pressurized or vacuum induced gas flow and guide it to or from the light application member 20 of the curing instrument 100. The light application member 20 may include a directional nozzle located at the tip of the light application member 20, and aimed in the direction of the illumination beam 64 to direct the gas flow either toward (pressurized gas) or away from (vacuum) the target surface being cured. The closed loop control of output from the light source 24 based on the optical sensor feedback signal to manage total energy actually delivered to the target surface may reduce the amount of heat energy delivered to the target surface as compared to conventional curing operations in which a total amount of light energy delivered from a device is preselected to be two to three times greater than that necessary in order to compensate for operator induced variation in the amount of light actually delivered. As a result, use of the coolant system 150 may be substantially avoided. Optionally, however, the coolant system 150 may be incorporated into the curing instrument 100 to offer the opportunity to operate at even higher levels of light intensity, thereby achieving a faster cure, without substantially allowing the resultant temperature rise at the target surface to climb to levels above a determined threshold.

In one embodiment, a method of manufacture of the curing instrument 100 may include assembling the light application member 20 by aligning the optical path 62 of the optical feedback sensor 28 with the optical path 64 of the light source 24. The method may include energizing the optical feedback sensor 28 such that light is emitted from the light input 58. The light input 58 may be disposed a) in proximity to a lens 50 that is mounted to the light source 24 and b) within a void or area defined between the lens 50 and another lens 52. The light source 24 may be energized to emit light at the same time as light is emitted from the light input 58. The optical feedback sensor 28 may be rotated and moved such that the side-fire termination corresponding to the light input 58 directs light along the optical path 62 within the optical path 64 of the light source 24. Once alignment between the optical path 62 in the optical path 64 has been achieved, the optical feedback sensor 28 may be affixed in place such that the light input 58 remains substantially stable with respect to the lens 50. In one embodiment, a calibration sensor system may detect the relative positions of the optical path 62 of the light input 58 and the optical path 64 of the light source 24 to facilitate alignment thereof. The light emitted from the light input 58 during a calibration or alignment may be of a type different from that emitted from the light source 24 to facilitate differentiating between the optical path 62 and the optical path 64.

Directional terms, such as "vertical," "horizontal," "top," "bottom," "upper," "lower," "inner," "inwardly," "outer" and "outwardly," are used to assist in describing the disclosure based on the orientation of the embodiments shown in the illustrations. The use of directional terms should not be interpreted to limit the present disclosure to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. A dental curing instrument for curing a target, the target including a restorative material that is curable in response to application of light energy, the dental curing instrument comprising:
  a light source capable of outputting the light energy to cure the restorative material, the light source being controllable to vary the light energy being output;
  a light sensor for sensing a light energy characteristic;
  an optical feedback path operable coupled to the light sensor, the optical feedback path being disposed to channel light reflected back from the target to the light sensor, wherein the light sensor is configured to sense the light energy characteristic with respect to the light reflected back from the target; and
  a controller operably coupled to the light sensor and the light source, the controller configured to vary, based on the light energy characteristic sensed by the light sensor, an operating characteristic of the light source from a first operating characteristic to a second operating characteristic to affect the light energy being output from the light source, wherein the light source is configured to output light based on operation at the first operating characteristic, wherein the light source is configured to output light based on operation at the second operating characteristic.

2. The dental curing instrument according to claim 1 wherein the optical feedback path is aligned with an illumination beam of light of the light source being output from the dental curing instrument such that the optical feedback path is within the illumination beam.

3. The dental curing instrument according to claim 2 wherein the optical feedback path is coaxially aligned with the illumination beam.

4. The dental curing instrument according to claim 3 wherein the light sensor is positioned to substantially avoid shadowing the illumination beam.

5. The dental curing instrument according to claim 1 wherein the optical feedback path and the light sensor form isolated optical feedback to the controller, wherein the controller is configured to assess, in real time, an actual light intensity (mW/cm2) delivered to a surface of the target, wherein the assessment is independent from operator induced variation caused by at least one of distance or angle of presentation of the dental curing instrument with respect to the target.

6. The dental curing instrument according to claim 1 wherein the light sensor provides a real time intensity optical sensor feedback signal, wherein the controller, based on the optical sensor feedback signal, produces corrective adjustments by controlling a light source intensity of the light source, whereby the controller stabilizes an actual light intensity delivered to a surface of the target.

7. The dental curing instrument of claim 6 wherein the controller is programmed to further use the optical sensor feedback signal as a basis for determining a time integral of an optical intensity on the target, the controller being programmed to compute, in real time, an actual total energy delivered to the surface of the target.

8. The dental curing instrument of claim 7 wherein the actual total energy is expressed in terms of energy in Joules/cm2 equaling intensity in w/cm2*tsec.

9. The dental curing instrument of claim 8 wherein the controller uses the real time computation of Joules/cm2 as a basis for controlling the light source to control an amount of energy delivered by further managing a time of active exposure.

10. The dental curing instrument of claim 1 wherein the optical feedback path is shared with a light delivery path through which the light source outputs energy to the target, wherein the controller is programmed to differentially and ratiometrically assess the light energy output from the light source and the light reflected back from the target, wherein signals indicative of the light energy output and the light reflected back are obtained from within the shared light delivery path.

11. The dental curing instrument of claim 1 further comprising Built In Diagnostics (BIT) based on the light energy characteristic.

12. The dental curing instrument of claim 11 wherein the BIT includes capabilities to detect at least one of light source issues, battery issues and tip contamination.

13. The dental curing instrument of claim 1 wherein the controller is configured to confirm that the target is present in a path of light energy output from the light source when a curing operation is being activated by a button, and in response to determining that the target is not present, deactivating the light source.

14. The dental curing instrument of claim 1 wherein the controller is programmed to determine presence and deactivate the light source in a timeframe on the order of microseconds.

15. The dental curing instrument of claim 1 wherein the target is a tooth or an opaque object.

16. A curing instrument for curing a light-curable material, said curing instrument comprising:
- a light source configured to generate light energy to cure the light-curable material, said light source configured to provide an illumination beam of light energy to the light-curable material;
- optical drive circuitry operably coupled to said light source, said optical drive circuitry configured to provide a power signal to said light source to generate said light energy, wherein said optical drive circuitry is configured to vary one or more operating characteristics of said power signal to vary output of light energy from said light source;
- a controller operably coupled to said optical drive circuitry, said controller configured to control operation of said optical drive circuitry to control generation of said light energy from said light source;
- an optical feedback sensor arranged to collect light reflected from the light-curable material, said optical feedback sensor having a light input with an optical sense path directed to the light-curable material, wherein said optical sense path of said light input is surrounded by said illumination beam generated from said light source; and
- a light sensor optically coupled to said light input of said optical feedback sensor, said light sensor is configured to generate an optical sensor feedback signal based on said light collected by said light input, wherein said controller directs said optical drive circuitry to vary, based on said optical sensor feedback signal, at least one of said one or more operating characteristics from a first operating characteristic to a second operating characteristic to vary output of light energy from said light source, wherein said light source is configured to output light based on operation at said first operating characteristic, wherein said light source is configured to output light based on operation at said second operating characteristic.

17. The curing instrument of claim 16 wherein said optical sense path is coaxially aligned with said illumination beam of light energy, wherein said light sensor is arranged relative to said light source to substantially avoid significant shadowing of said illumination beam.

18. The curing instrument of claim 16 further comprising a gas channel coupled to a gas nozzle that directs gas over the light-curable material to affect a temperature of the light-curable material, said gas channel forming at least part of a coolant system.

* * * * *